(12) United States Patent
Mori

(10) Patent No.: US 8,874,417 B2
(45) Date of Patent: Oct. 28, 2014

(54) METHOD OF DERIVING SCATTERED WAVE, METHOD OF MANUFACTURING LENS, AND NON-TRANSITORY RECORDING MEDIUM

(75) Inventor: Taisei Mori, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 372 days.

(21) Appl. No.: 13/449,373

(22) Filed: Apr. 18, 2012

(65) Prior Publication Data

US 2012/0260493 A1   Oct. 18, 2012

(30) Foreign Application Priority Data

Apr. 18, 2011   (JP) .................. 2011-091905

(51) Int. Cl.
*G06G 7/48* (2006.01)
*G01N 21/47* (2006.01)
*B82Y 20/00* (2011.01)

(52) U.S. Cl.
CPC ............... *G01N 21/47* (2013.01); *B82Y 20/00* (2013.01)
USPC .......................................................... 703/6

(58) Field of Classification Search
USPC ............................... 703/6; 250/234; 359/564
See application file for complete search history.

(56) References Cited

U.S. PATENT DOCUMENTS 4,067,645 A * 1/1978 Carlson et al. ................ 359/564
6,911,646 B1 * 6/2005 Weitekamp .................. 250/234

OTHER PUBLICATIONS

Nieminen et al., "Computational modeling of optical tweezers", Optical Trapping and Optical Micromanipulation, Proceedings of SPIE, 2004.*
Yang, H., "Single particle light scattering: Imaging and dynamical fluctuations in the polarization and spectral response", American Chemical society, 2007.*
Meisner, R., "Production and characterization of functional nanoparticles synthesized in Plasmas", der Ruhr Universitat, Bochum, 2009.*
Nieminen et al., "T-matrix method for modelling optical tweezers", Journal of Modern Optics, Mar. 2011.*
Tausendfreund et al, "Simulation of light scattering from surfaces containing spherical and elliptical nanoparticles", Proceedings of SPIE, 2006.*
Kozen, M., "cCharacterization of colloidal nanoparticle aggregates using light scattering techniques", University of Kentucky, 2007.*

(Continued)

*Primary Examiner* — Kandasamy Thangavelu
(74) *Attorney, Agent, or Firm* — Rossi, Kimms & McDowell LLP

(57) ABSTRACT

A method of deriving a scattered wave includes the steps of calculating a first scattered wave from a scatterer at a predetermined position by using a predetermined electromagnetic wave entering the scatterer, calculating a second scattered wave from a spherical nanoparticle cluster at the predetermined position by using T-matrix method when the predetermined electromagnetic wave enters the spherical nanoparticle cluster in a state where the spherical nanoparticle cluster containing a plurality of spherical nanoparticles is arranged inside a region that has the same shape and size as those of the scatterer, determining a condition of the plurality of spherical nanoparticles so that the first scattered wave is equal to the second scattered wave, and obtaining the scattered wave from the scatterer at an arbitrary position when an arbitrary electromagnetic wave enters the scatterer, based on the determined condition of the spherical nanoparticle.

8 Claims, 8 Drawing Sheets

(56) References Cited

OTHER PUBLICATIONS

Margueritat, J, "Optical and vibrational properties of new "Nano-Designed" materials produced by pulsed laser deposition", Universidad Autonoma de Madrid, 2008.*

Sekhar Das, H., "Photopolarimetric studies of comets and other objects", Assam University, 2004.*

Johnson, B.R., "Invariant imbedding T matrix approach to electromagnetic scattering", Applied optics, 1988.*

Alu et al., "Plasmonic and metamaterial clocking: Physical mechanisms and potentials", Journal of optics A: Pure and applied optics, 2008.*

Borghese et al. "Optical trapping of nonsherical particle in the T-matrix formalism", Optics Express, 2007.*

Gantzounis, G. "Plasmon Modes of Axisymmetric Metallic Nanoparticles: A Group Theory Analysis", American Chemical society, 2009.*

Wriedt et al.; "Light scattering by single erythrocyte: Comparison of different methods", Journal of Quantitative Spectroscopy & Radiative Transfer 100; pp. 444-456, 2006.

Thomas Wriedt; "Using T-Matrix for Light Scattering Computations by Non-axisymmetric Particles: Superellisoids and Realistically Shaped Particles", Istitut für Werkstofftechnik, Badgasteiner Str. 3, 28359 Bremen, Germany; pp. 1-34, Jan. 28, 2002.

Kawano et al.; "Numerical Analysis of three Dimensional Multiple Scattering from Variously Shaped Objects Using the Yasura Method", ISAP, 2004, pp. 153-156.

* cited by examiner

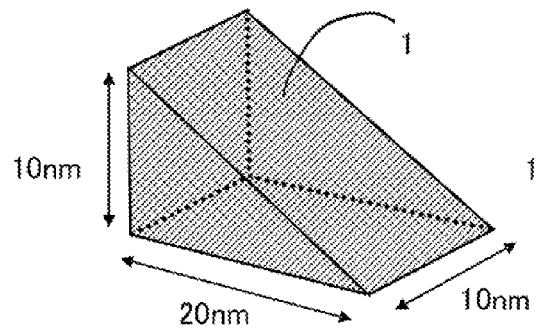
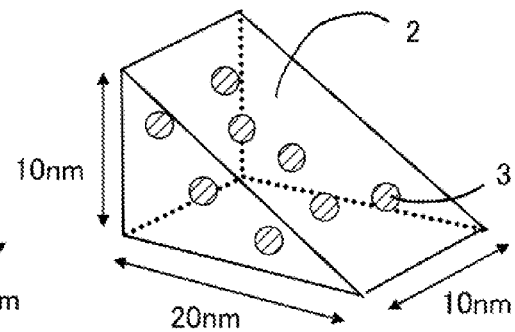
FIG. 2A                FIG. 2B
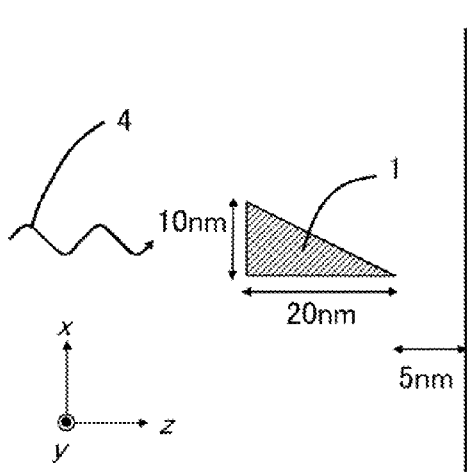
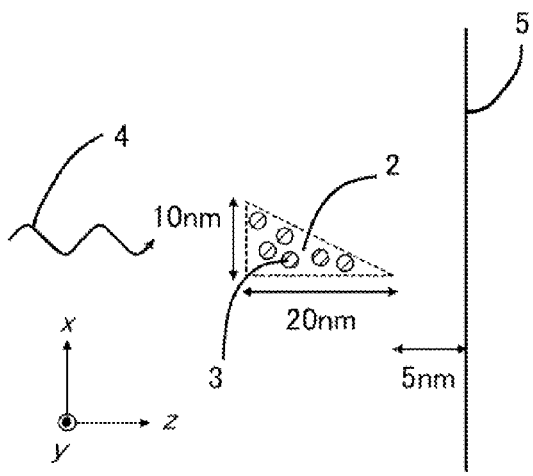
FIG. 3A                FIG. 3B

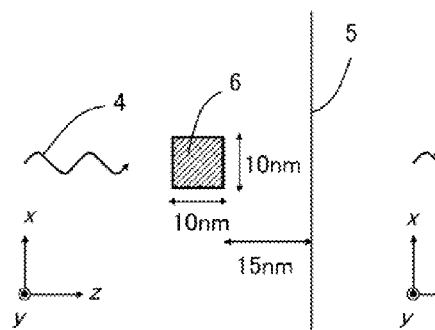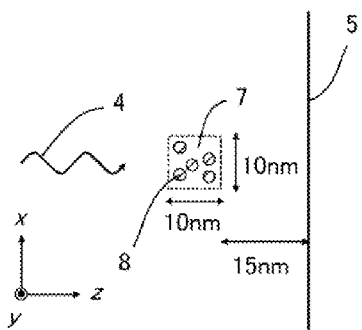
FIG. 6A  FIG. 6B
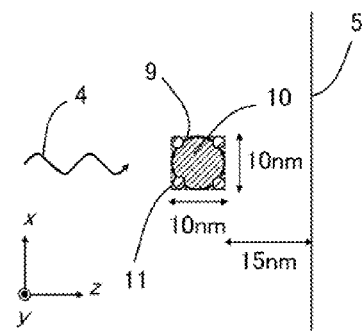
FIG. 6C
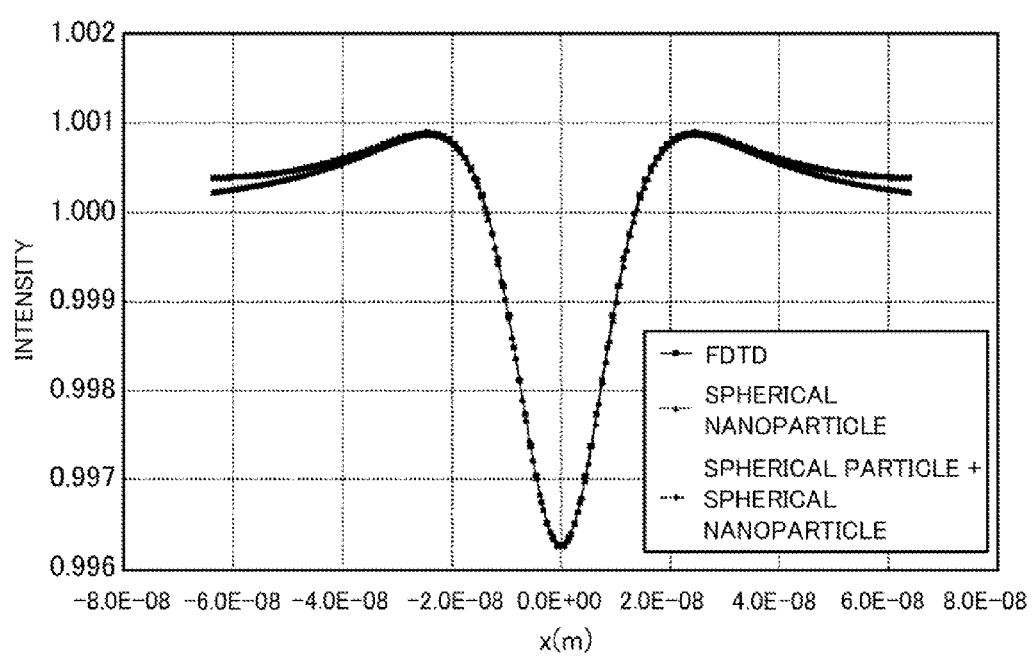
FIG. 7

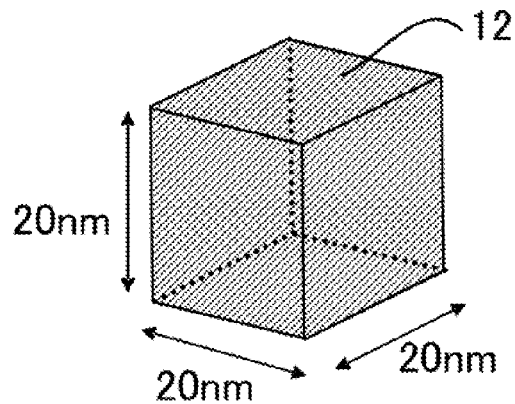
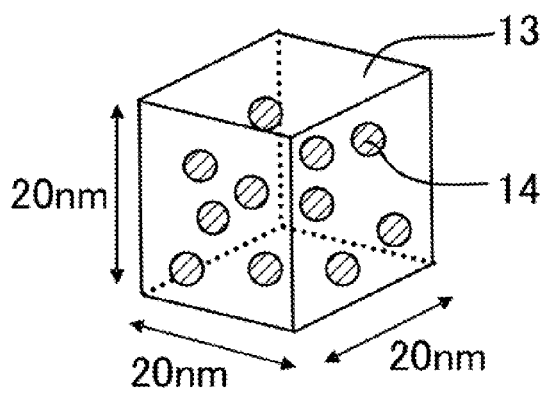
FIG. 8A  FIG. 8B
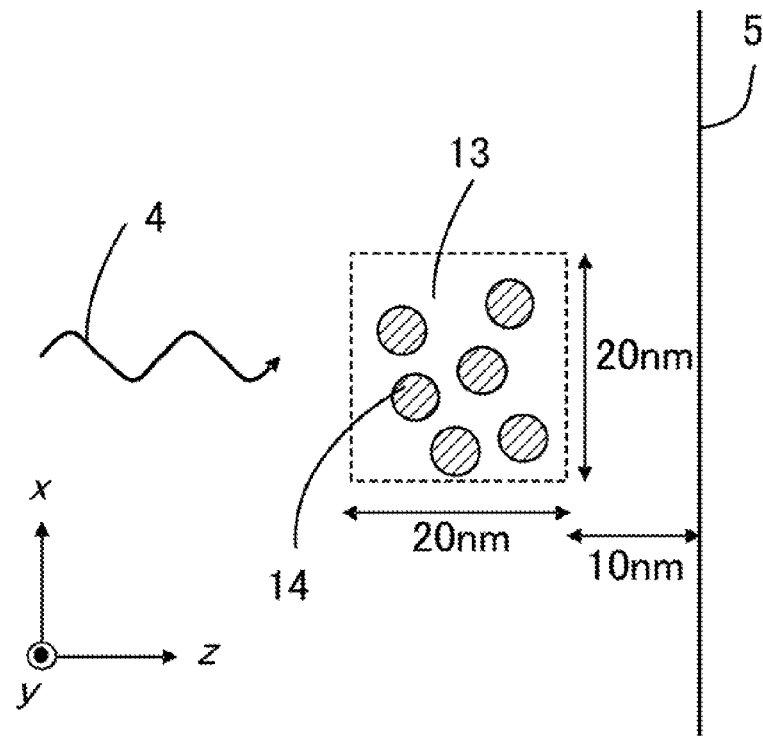
FIG. 9

METHOD OF DERIVING SCATTERED WAVE, METHOD OF MANUFACTURING LENS, AND NON-TRANSITORY RECORDING MEDIUM

BACKGROUND OF THE INVENTION

1. Field of the Invention

The present invention relates to a method of deriving a scattered wave using T-matrix method.

2. Description of the Related Art

In various optical fields, a method of deriving a scattered wave from a scatterer having a size smaller than a wavelength is known. For example, according to a derivation method by Mie scattering, the scattered wave generated by a spherical particle can be derived at high speed and with high accuracy. In a method of deriving an electromagnetic field that is represented by FDTD method (Finite-difference time-domain method) or a boundary element method, whole or a part of a derivation region is divided in a mesh manner, and a dielectric constant is defined for all of the grating points to perform a propagation calculation of light.

T. Wriedt et al., "Light scattering by single erythrocyte: Comparison of different methods" discloses DDA (discrete-dipole approximation) method, which treats a scatterer as a cluster of dipoles to be divided to be able to handle the scatterer having an arbitrary shape. T. Wriedt et al., "Light scattering by single erythrocyte: Comparison of different methods", and T. Wriedt, "Using the T-Matrix Method for Light Scattering Computations by Non-axisymmetric Particles: Superellipsoids and Realistically Shaped Particles" discloses T-matrix method that is capable of strictly handing a multiple scattering generated by spherical particles, and it also discloses the T-matrix method that is applicable to an aspherical particle.

However, in the derivation method of the scattered wave using a conventional derivation method of an electromagnetic wave, it can be derived only on a limited condition. For example, in a method using the Mie scattering, a perfect sphere is only handled, and a multiple scattering when a plurality of particles exist cannot be handled. In addition, due to a derivation cost, a model may be significantly limited depending on a method in accordance with a computer environment. For example, in the derivation method of the electromagnetic wave that is represented by the FDTD method or the boundary element method, since whole or a part of the derivation region needs to be divided in the mesh manner, a derivation time or a consumption amount of a memory in a computer is enormous. In the DDA, since a fine dipole needs to be closely arranged inside the scatterer, the derivation cost is enormous. Thus, the number of the settable scatterers is limited, and there may be a case where the mesh division enough to express the fine structure of the scatterer or the arrangement of the dipole is impossible. Recently, as disclosed in T. Wriedt et al., "Light scattering by single erythrocyte: Comparison of different methods", and T. Wriedt, "Using the T-Matrix Method for Light Scattering Computations by Non-axisymmetric Particles: Superellipsoids and Realistically Shaped Particles", there is a derivation method that can also be applied to an aspherical particle by the improvement of the T-matrix method, but it can only handle a particle having a shape similar to a spherical shape such as an ellipsoid.

SUMMARY OF THE INVENTION

The present invention provides a method of deriving a scattered wave capable of deriving the scattered wave from a scatterer having an arbitrary shape at highspeed and with high accuracy, a method of manufacturing a lens using the method of deriving the scattered wave, and a non-transitory recording medium.

A method of deriving a scattered wave as one aspect of the present invention includes the steps of calculating a first scattered wave from a scatterer at a predetermined position by using a predetermined electromagnetic wave entering the scatterer, calculating a second scattered wave from a spherical nanoparticle cluster at the predetermined position by using T-matrix method when the predetermined electromagnetic wave enters the spherical nanoparticle cluster in a state where the spherical nanoparticle cluster containing a plurality of spherical nanoparticles is arranged inside a region that has the same shape and size as those of the scatterer, determining a condition of the plurality of spherical nanoparticles so that the first scattered wave is equal to the second scattered wave, and obtaining the scattered wave from the scatterer at an arbitrary position when an arbitrary electromagnetic wave enters the scatterer, based on the determined condition of the spherical nanoparticle.

A method of manufacturing a lens as another aspect of the present invention includes the step of deriving a scattered wave of the lens containing the nanoparticle as a scatterer using the method of deriving the scattered wave.

A non-transitory recording medium as another aspect of the present invention records a program that is configured so that the method of deriving the scattered wave is executed by a computer.

Further features and aspects of the present invention will become apparent from the following description of exemplary embodiments with reference to the attached drawings.

BRIEF DESCRIPTION OF THE DRAWINGS

FIGS. 2A and 2B are schematic diagrams of illustrating a scatterer and a spherical nanoparticle cluster in a first embodiment.

FIGS. 3A and 3B are arrangement diagrams of the scatterer and the spherical nanoparticle cluster in the first embodiment.

FIGS. 6A to 6C are arrangement diagrams of the scatterer, the spherical nanoparticle cluster, and the spherical particle in the second embodiment.

FIG. 7 is a diagram of illustrating intensities of scattered waves generated by the scatterer, the spherical nanoparticle cluster, and a combination of the spherical particle and the spherical nanoparticle cluster.

FIGS. 8A and 8B are schematic diagrams of a scatterer and a spherical nanoparticle cluster in a third embodiment.

FIG. 9 is an arrangement diagram of the spherical nanoparticle cluster in the third embodiment.

DESCRIPTION OF THE PREFERRED EMBODIMENTS

Figure 1:
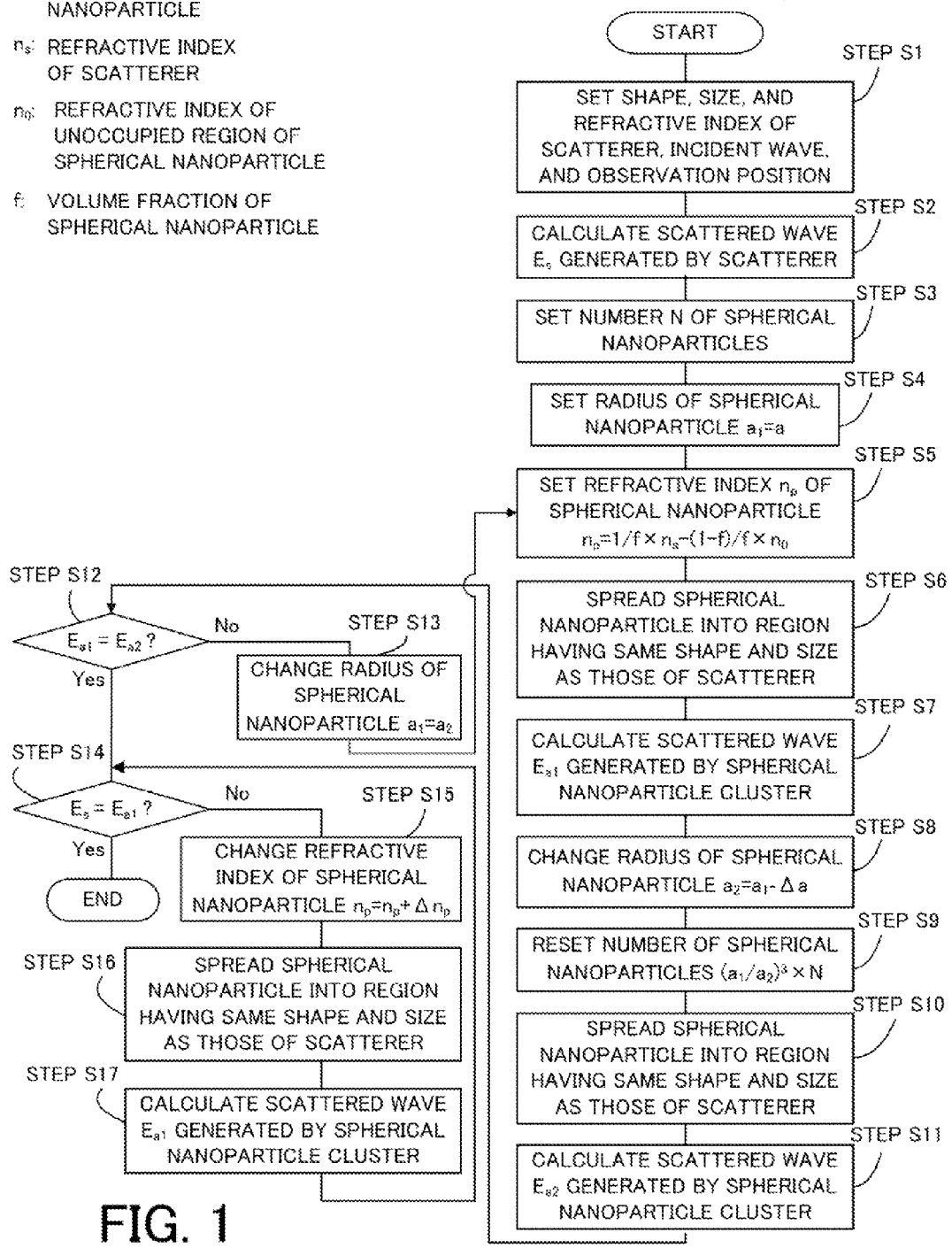
FIG. 1 is a flowchart of a method of deriving a scattered wave in each of the present embodiments.

Exemplary embodiments of the present invention will be described below with reference to the accompanied drawings. In each of the drawings, the same elements will be denoted by the same reference numerals and the duplicate descriptions thereof will be omitted.

T-matrix method is a well-known method, which represents a scattered wave using a spherical vector function for a spherical particle to be able to exactly derive the scattered wave without any approximation. In addition, it can also derive an exact scattered wave without any approximation using the spherical vector function for a multiple scattering on condition that a plurality of spherical particles exist. The scattered wave of the scatterer is derived by treating the scatterer having an arbitrary shape as a cluster of spherical nanoparticles and by using the T-matrix method for the spherical nanoparticle. In this case, since it is necessary that a parameter of the spherical nanoparticle is derived so that the scattered wave generated by the scatterer is equal to a scattered wave generated by the spherical nanoparticle, the scattered wave of the scatterer needs to be calculated using another method. Once the parameter of the spherical nanoparticle is calculated, the scattered wave can be derived using the T-matrix method at high speed even when a polarization state of an electromagnetic field that enters the scatterer or an incidence angle is changed.

Next, referring to FIG. 1, a method of deriving the scattered wave in the present embodiment will be described. FIG. 1 is a flowchart of the method of deriving the scattered wave in the present embodiment, which is a flowchart of determining conditions of the spherical nanoparticle (conditions related to a radius of the spherical nanoparticle, the number of the spherical nanoparticles, and a refractive index of the spherical nanoparticle) in the method of deriving the scattered wave. First of all, in Step 1, various conditions such as a shape, a size, and a refractive index of the scatterer that generates the scattered wave, an incident electromagnetic wave (an incident wave), and an observation position of the scattered wave are set. In Step S2, the electromagnetic wave set in Step 1 enters the scatterer, and a scattered wave $E_s$ generated by the scatterer at the observation position set in Step 1 is calculated. In the present embodiment, the scattered wave $E_s$ is calculated using FDTD method (Finite-difference time-domain method), but the embodiment is not limited to this and other methods may also be used. Thus, in Steps 1 and 2, a predetermined electromagnetic wave enters the scatterer, and the scattered wave $E_s$ (a first scattered wave) from the scatterer at a predetermined position is calculated.

Subsequently, in Step S3, the number N of the spherical nanoparticles is set. The value of N is arbitrarily set, but it is limited in view of the calculation time or the environment of a computer. In Step S4, a radius "a" ($a_1$=a) of the spherical nanoparticle is set. As a size (radius a) of the spherical nanoparticle, an arbitrary value that is smaller than the size of the scatterer is used, but it is preferred that it be smaller or equal to 1/10 of the size of the scatterer. In Step S5, a refractive index $n_p$ of the spherical nanoparticle is set. First of all, a volume fraction f of the spherical nanoparticle that occupies a volume of the scatterer is obtained using a volume of the scatterer, a radius a of the spherical nanoparticle, and the number N of the spherical nanoparticles. Then, using a refractive index $n_s$ of the scatterer, a refractive index $n_0$ of a region that contains the spread (arranged) spherical nanoparticle and that is not occupied by the spherical nanoparticle, and the volume fraction f, the refractive index $n_p$ of the spherical nanoparticle is derived as $n_p = 1/f \times n_s - (1-f)/f \times n_0$. An initial value of the refractive index $n_p$ of the spherical particle is, for example, set so that an effective refractive index determined by the refractive index $n_p$ of the spherical nanoparticle and the volume fraction f coincides with the refractive index $n_s$ of the scatterer.

Subsequently, in Step S6, a region that has the same shape and size as those of the scatterer is set, and a spherical nanoparticle cluster that contains a plurality of spherical nanoparticle is spread (arranged) inside the region. The spread position of the spherical nanoparticle is determined using a random number at random. In Step S7, the electromagnetic wave (the incident wave) set in Step S1 enters the spherical nanoparticle having a radius $a_1$, and a scattered wave $E_{a1}$ (a second scattered wave) from the spherical nanoparticle cluster at the observation position set in Step S1 is calculated using the T-matrix method. In Step S8, the radius a of the spherical nanoparticle is changed, and a radius $a_2 = a_1 - \Delta a$ that is smaller than the value (radius $a_1$) set in Step S4 is set. In Step S9, the number N of the spherical nanoparticles is reset to $(a_1/a_2)^3 \times N$ so that the volume fraction f of the spherical nanoparticle calculated in Step S5 is constant. In this case, in order to set the number of the spherical nanoparticles within the limitation of the calculation time or the environment of the computer, it is preferred that a radius $a_2$ of the spherical nanoparticle changed in Step S8 be set to be a value closer to the original radius $a_1$.

Subsequently, in Step S10, the spherical nanoparticle set in Steps 8 and 9 is spread into a region having the same shape and size as those of the scatterer. In Step S11, the incident electromagnetic wave set in Step S1 enters the spherical nanoparticle having the radius $a_2$, and a scattered wave $E_{a2}$ of the spherical nanoparticle at the observation position set in Step S1 is calculated using the T-matrix method. In Step S12, the scattered wave $E_{a1}$ obtained in Step S7 is compared with the scattered wave $E_{a2}$ obtained in Step S11. When the scattered waves $E_{a1}$ and $E_{a2}$ of the spherical nanoparticle before and after the change of the radius (radii $a_1$ and $a_2$) are not equal to each other ($E_{a1} \neq E_{a2}$), the radius $a_2$ of the spherical nanoparticle after the change is changed to the radius $a_1$ of the spherical nanoparticle before the change in Step S13, and the flow returns to Step S5. Thus, the radius of the spherical nanoparticle is determined so that the scattered wave of the spherical nanoparticle cluster does not change when the radius of the spherical nanoparticle is reduced and the number of the spherical nanoparticles is increased on condition that the volume fraction of the spherical nanoparticle cluster is constant with respect to the volume of the region.

On the other hand, in Step S12, when the scattered waves of the spherical nanoparticle before and after the change of the radius are equal to each other ($E_{a1} = E_{a2}$), the flow proceeds to Step S14. With respect to the term "the scattered waves of the spherical nanoparticle before and after the change of the radius are equal to each other", it is assumed that the scattered waves are equal to each other if a difference of the scattered waves of each other is within a predetermined threshold value. This predetermined threshold value may be changed in accordance with an accuracy of deriving (obtaining) the scattered wave from the scatterer (an object or a material to be tested). It is natural that the threshold value is decreased when the derivation accuracy of the scattered wave needs to be improved, and on the other hand the threshold value is increased when the time required for deriving the scattered wave (the calculation time by the computer or the like) needs to be reduced even though the derivation accuracy of the scattered wave is deteriorated. Anyway, however, it is preferred that the threshold value be smaller than the initial value. The difference of the scattered waves may be a volume of a space between the two scattered waves, or alternatively it may be a sum or an average value of the differences (distances) of the scattered waves at a plurality of positions, or it may be a difference of the scattered waves (the distance) at a specific position.

In Step S14, the scattered wave $E_s$ (the first scattered wave) generated by the scatterer obtained in Step S2 is compared with the scattered wave $E_{a1}$ (the second scattered wave) generated by the spherical nanoparticle obtained in Step S7. When the scattered wave $E_s$ generated by the scatterer is not equal to the scattered wave $E_{a1}$ generated by the spherical nanoparticle ($E_s \neq E_{a1}$), the flow proceeds to Step S15. In Step S15, the refractive index $n_p$ of the spherical nanoparticle is changed to a refractive index $n_p + \Delta n_p$. Subsequently, in Step S16, the spherical nanoparticle is spread into a region having the same shape and size as those of the scatterer. Then, in Step S17, the incident electromagnetic wave set in Step S1 enters the spherical nanoparticle and the scattered wave $E_{a1}$ generated by the spherical nanoparticle at the observation position set in Step S1 is calculated using the T-matrix method, and then the flow returns to Step S14. On the other hand, in Step S14, when the scattered wave $E_s$ generated by the scatterer is equal to the scattered wave $E_{a1}$ generated by the spherical nanoparticle ($E_s = E_{a1}$), the flow is finished. Whether or not the scattered waves in this case are equal to each other is similar to the case of Step S12.

Thus, in the derivation method, the plurality of conditions of the spherical nanoparticle (the conditions of the radius of the spherical nanoparticle, the number of the spherical nanoparticles, and the refractive index of the spherical nanoparticle) are determined (Steps S9, S13, and S15) so that the first scattered wave is equal to the second scattered wave (Step S14). Then, using the determined conditions of the spherical nanoparticle, an arbitrary electromagnetic wave enters the scatterer to derive (calculate or obtain) the scattered wave from the scatterer at an arbitrary position.

In the present embodiment, the radius of the spherical nanoparticle is set after the number of the spherical nanoparticles is set and finally the refractive index of the spherical nanoparticle is set, but the embodiment is not limited to this and these three parameters can be set in an arbitrary order. In order to improve the calculation accuracy, as a value of the scattered wave generated by the spherical nanoparticle, an arrangement of the spherical nanoparticle may also be changed to adopt an average value of the scattered wave obtained from multiple calculations.

First Embodiment

Figure 4:
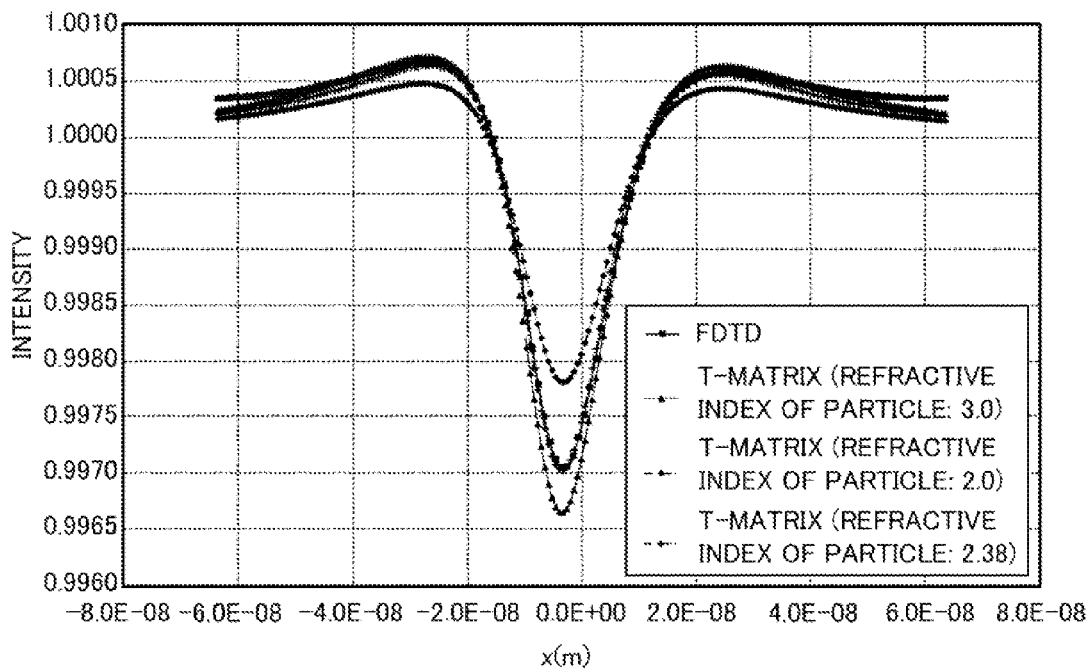
FIG. 4 is a diagram of illustrating intensities of scattered waves generated by the scatterer and the spherical nanoparticle cluster in the first embodiment.

Next, a first embodiment of the present invention will be described. FIGS. 2A and 2B are schematic diagrams of a scatterer and a spherical nanoparticle cluster in the present embodiment. FIG. 2A illustrates a scatterer 1 that has a shape of a triangle pole, and FIG. 2B illustrates a state in which a spherical nanoparticle cluster 3 (a plurality of spherical nanoparticles) is spread (arranged) inside a triangle pole region 2 that has the same shape and size as those of the scatterer 1. FIGS. 3A and 3B are arrangement diagrams of the scatterer and the spherical nanoparticle cluster. FIG. 3A illustrates an arrangement in which an incident wave 4 (an electromagnetic wave) enters the scatterer 1 to calculate the scattered wave, and FIG. 3B illustrates a state in which the scatterer 1 is replaced with the spherical nanoparticle cluster 3. FIG. 4 is a diagram of illustrating intensities of the scattered waves generated by the scatterer 1 and the spherical nanoparticle cluster 3.

As illustrated in FIG. 3A, the incident wave 4 has an x polarization, and an observation line 5 in an x direction is set at a position distant from the scatterer 1 by 5 nm in a z direction. In the present embodiment, the intensity of an x component of the electromagnetic field is obtained on the observation line 5. In the present embodiment, the electromagnetic field is calculated using the FDTD method, but the embodiment is not limited to this and other methods can also be used. Furthermore, in the present embodiment, the arrangement as illustrated in FIG. 3B is adopted to calculate the electromagnetic field on the observation line 5 using the T-matrix method.

TABLE 1

| LENGTH (nm) OF SCATTERER (TRIANGLE POLE) | WIDTH (nm) OF SCATTERER (TRIANGLE POLE) | HEIGHT (nm) OF SCATTERER (TRIANGLE POLE) |
|---|---|---|
| 10.0 | 20.0 | 10.0 |
| REFRACTIVE INDEX OF SCATTERER | RADIUS (nm) OF SPHERICAL NANOPARTICLE | VOLUME FRACTION OF SPHERICAL NANOPARTICLE |
| 1.1 | 0.5 | 0.1 |

Table 1 indicates parameters that are used for the calculation in the present embodiment. The scatterer 1 is a triangle pole that has a length of 10 nm, a width of 20 nm, and a height of 10 nm with a refractive index of 1.1. In this case, the intensity of the electromagnetic field in the x direction of the scatterer 1 on the observation line (the intensity of the scattered wave generated by the scatterer) is illustrated as FDTD in FIG. 4. In the present embodiment, the number of the spherical nanoparticles spread into the inside of the triangle pole area 2 that has the same shape and size as those of the scatterer 1 is set to 190. The radius of the spherical nanoparticle is set to 0.5 nm. As a result, a volume ratio of a region of the spherical nanoparticle cluster 3 and a region that is inside the triangle pole region 2 and that is not occupied by the spherical nanoparticle cluster 3 is 0.1:0.9. When the refractive index of the spherical nanoparticle cluster 3 is obtained using the expression illustrated in Step 5 of FIG. 1 so that the entire refractive index is equal to 1.1, the refractive index of the spherical nanoparticle cluster 3 is equal to 2.0 and it is set to be an initial value. In this case, it is assumed that the region that is inside the triangle pole region 2 and that is not occupied by the spherical nanoparticle cluster 3 is a vacuum, and the refractive index of the region is 1.0. The intensity of the electromagnetic field in the x direction of the scattered wave of the spherical nanoparticle cluster 3 (the scattered wave generated by the spherical nanoparticle cluster 3) on the observation line 5 calculated in this condition is illustrated as T-MATRIX (REFRACTIVE INDEX OF PARTICLE: 2.0) in FIG. 4.

Next, the radius of the spherical nanoparticle is changed from 0.5 nm to 0.45 nm and the number of the spherical nanoparticles is set to 260 so that the volume fraction of the spherical nanoparticle cluster 3 with respect to the triangle pole region 2 is constant. In this case, the intensity of the electromagnetic field of the scattered wave in the x direction on the observation line 5 does not change compared to the result obtained when the radius is set to 0.5 nm. Therefore, values that are the number of the spherical nanoparticles of 190 and the radius of 0.5 nm are adopted. In FIG. 4, the intensity of the T-MATRIX (THE REFRACTIVE INDEX OF THE PARTICLE: 2.0) is higher than that of the FDTD, and thus the both results do not coincide with each other. On the other hand, when the refractive index of the spherical nanoparticle cluster 3 is set to 3.0 to derive the scattered wave similarly, the result indicated by the T-MATRIX (THE REFRACTIVE INDEX OF THE PARTICLE: 3.0) in FIG. 4 is obtained, which is lower than that of the FDTD. As a result, the refractive index of the spherical nanoparticle cluster 3 in which the scattered waves generated by the scatterer 1 and the spherical nanoparticle cluster 3 coincide with each other exists between 2.0 and 3.0.

Subsequently, when the refractive index of the spherical nanoparticle cluster 3 is changed from 2.0 to 3.0 by 0.1, the intensity of the scattered wave in the refractive index of 2.3 is higher than the result of the FDTD, and on the other hand the intensity in the refractive index of 2.4 is lower than the result. As a result, the refractive index of the spherical nanoparticle cluster 3 exists between 2.3 and 2.4. Therefore, when the refractive index of the spherical nanoparticle cluster 3 is changed from 2.3 to 2.4 by 0.01, the intensity of the scattered wave coincides with the result of the FDTD when the refractive index is set to 2.38. As illustrated in FIG. 4, both results coincide with each other when the refractive index of the spherical nanoparticle cluster 3 is 2.38.

Second Embodiment

Next, a second embodiment of the present invention will be described. The present embodiment spreads spherical nanoparticles having two sizes different from each other to be able to derive the scattered wave generated by the spherical nanoparticles at high speed. In other words, in the present embodiment, the spherical nanoparticle cluster contains at least a first spherical nanoparticle and a second spherical nanoparticle larger than the first spherical nanoparticle.

Figure 5A:
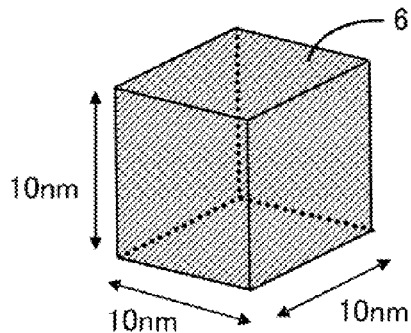
FIGS. 5A and 5C are diagrams of a scatter, a spherical nanoparticle cluster, and a spherical particle in a second embodiment.
Figure 5B:
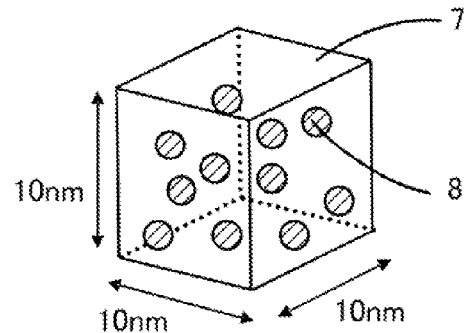
Figure 5C:
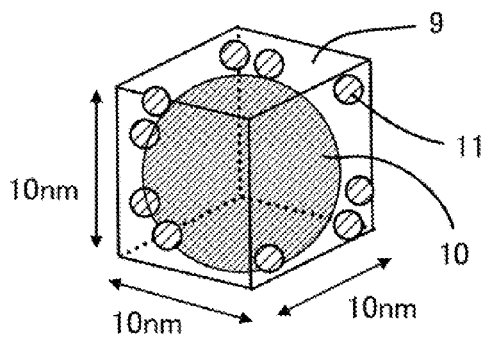

FIGS. 5A to 5C are schematic diagrams of a scatterer, a spherical nanoparticle cluster, and a spherical particle in the present embodiment. FIG. 5A illustrates a scatterer 6 that has a cubic shape, and FIG. 5B illustrates a state in which a spherical nanoparticle cluster 8 (a plurality of spherical nanoparticles) is spread (arranged) inside a cubic region 7 that has the same shape and size as those of the scatterer 6. FIG. 5C illustrates a state in which a spherical particle 10 (a second spherical nanoparticle) that has the same diameter as one side of the scatterer 6 (the cube) is disposed inside the cubic region 9 that has the same shape and size as those of the scatterer 6. In addition, in FIG. 5C, a spherical nanoparticle cluster 11 (a plurality of first spherical nanoparticles) is spread (arranged) in a region that is inside the cubic region 9 and that is not occupied by the spherical particle 10.

FIGS. 6A to 6C are arrangement diagrams of the scatterer, the spherical nanoparticle cluster, and the spherical particle. FIG. 6A illustrates an arrangement in which an incident wave 4 (an electromagnetic wave) enters the scatterer 6 to calculates the scattered wave, and FIG. 6B illustrates a state in which the scatterer 6 is replaced with the spherical nanoparticle cluster 8. FIG. 6C illustrates a state in which the scatterer 6 is replaced with the spherical particle 10 (the second spherical particle) and the spherical nanoparticle cluster 11 (the first spherical particle). FIG. 7 is a diagram of illustrating intensities of the scattered waves generated by the scatterer 6, the spherical nanoparticle cluster 8, and the combination of the spherical particle 10 and the spherical nanoparticle cluster 11.

As illustrated in FIG. 6A, the incident wave 4 has an x polarization, and an observation line 5 in an x direction is set at a position distant from the scatterer 6 by 15 nm in a z direction. In the present embodiment, the intensity of an x component of the electromagnetic field (the intensity of the scattered wave) on the observation line 5 is derived. In the present embodiment, the calculation is performed using the FDTD method, but the embodiment is not limited to this and other methods may also be used. FIGS. 6B and 6C illustrate states in which the scatterer 6 of FIG. 6A is replaced with the configurations of FIGS. 5B and 5C respectively, and the intensities of these scattered waves are calculated by using the T-matrix method.

TABLE 2

| ONE SIDE (nm) OF SCATTERER (CUBE) | REFRACTIVE INDEX OF SCATTERER | RADIUS (nm) OF SPHERICAL NANO-PARTICLE | VOLUME FRACTION OF SPHERICAL NANOPARTICLE |
|---|---|---|---|
| 10.0 | 1.1 | 0.5 | 0.1 |

| RADIUS (nm) OF LARGE SPHERICAL PARTICLE | REFRACTIVE INDEX OF LARGE SPHERICAL PARTICLE |
|---|---|
| 5.0 | 1.1 |

Table 2 indicates parameters that are used for the calculation in the present embodiment. The scatterer 6 is a cube that has each side of 10 nm and a refractive index of 1.1. In this case, the intensity of the electromagnetic field in the x direction of the scatterer 6 on the observation line 5 (the intensity of the scattered wave generated by the scatterer) is indicated as FDTD in FIG. 7. In FIG. 6B, the intensity of the electromagnetic field is calculated by the process similar to that of the first embodiment. The result is indicated as SPHERICAL NANOPARTICLE in FIG. 7. Since the shape of the scatterer in the present embodiment is different from the case of the first embodiment, the intensity coincides with the case of FDTD when the refractive index of the spherical nanoparticle cluster 8 is set to 2.65.

Next, in FIG. 6C, the spherical particle 10 that is in internal contact with the cubic region 9 having the same size as that of the scatterer 6 is arranged. The refractive index of the spherical particle 10 has the same refractive index of 1.1 as that of the scatterer 6. Furthermore, 90 spherical nanoparticles (the spherical nanoparticle cluster 11) are spread in the region that is inside the cubic region 9 and that is not occupied by the spherical particle 10. The radius of the spherical nanoparticle is set to 0.5 nm. As a result, the ratio of a volume of the spherical nanoparticle cluster 11 and a volume of the region that is inside the cubic region 9 and that is not occupied by any of the spherical particle 10 and the spherical nanoparticle cluster 11 is 0.1:0.9. When the refractive index of the spherical nanoparticle cluster 11 is calculated using the expression illustrated in Step S5 of FIG. 1 so that the refractive index of the region that is inside the cubic region 9 and that is not occupied by the spherical particle 10 is 1.1, the refractive index is 2.0 and this is set as an initial value. In this case, in Step S5, the scatterer region is calculated on the assumption that the region that is inside the cubic region 9 and that is not occupied by any of the spherical particle 10 and the spherical nanoparticle cluster 11 is a vacuum, and the refractive index is set to 1.0. As a result, an entire refractive index that is calculated based on the ratio of a volume of the spherical particle 10 inside the cubic region 9, a volume of the spherical nanoparticle cluster 11, and a volume of the region that is inside the cubic region 9 and that is not occupied by any of the spherical particle 10 and the spherical nanoparticle cluster 11 is also set to 1.1.

First of all, the intensity of the electromagnetic field in the x direction of the scattering generated by the cubic region 9 (the intensity of the scattered light) on the observation line 5 in this condition is derived. Next, the radius of each spherical nanoparticle of the spherical nanoparticle cluster 11 is changed from 0.5 nm to 0.45 nm and the number of the spherical nanoparticles is set to 123 so that the volume fraction of a mixed particle cluster of the spherical particle 10 and the spherical nanoparticle cluster 11 with respect to the cubic region 9 is constant. In this case, since the intensity of the electromagnetic field in the x direction of the scattering on the observation line 5 (the intensity of the scattered light) does not change compared to the result of the case in which the radius of the spherical nanoparticle is 0.5 nm, values that are the number of the spherical nanoparticles of 90 and the radius of 0.5 nm are adopted. The result of the electromagnetic calculation (the intensity of the scattered light) when the process similar to that of the first embodiment is performed in this condition is indicated as SPHERICAL PARTICLE+ SPHERICAL NANOPARTICLE in FIG. 7. Since this case is different from the case of FIG. 6B and both the spherical particle and the spherical nanoparticle are arranged, it coincides with the FDTD when the refractive index of the spherical nanoparticle cluster 11 is set to 2.75.

TABLE 3

| | COMPUTER SPECIFICATION | CALCULATION TIME |
| --- | --- | --- |
| ONLY SPHERICAL NANOPARTICLE | Dual-Core AMD Opteron ™ Processor 2220 2.8 GHz | 14 MINUTES 51 SECONDS |
| LARGE SPHERICAL PARTICLE + SPHERICAL NANOPARTICLE | | 5 MINUTES 13 SECONDS |

Table 3 indicates a specification of the computer used for deriving the electromagnetic field and a time required for deriving the electromagnetic field in the present embodiment. The derivation time in the mixture of the spherical particle 10 and the spherical nanoparticle cluster 11 is as 2.8 times as fast as the time when only the spherical nanoparticle cluster 8 is contained. However, this derivation time does not include the time required for setting the parameters of the spherical nanoparticle cluster 11.

Third Embodiment

Next, a third embodiment of the present invention will be described. The present embodiment changes a particle arrangement of a spherical nanoparticle to obtain an average value of scattered waves to derive the scattered wave. In other words, a spherical nanoparticle cluster is arranged multiple times at random to calculate the average value of the scattered waves from the spherical nanoparticle cluster using the T-matrix method, and this average value is set to be the second scattered wave. Therefore, according to the present embodiment, the scattered wave can be derived more precisely.

Figure 10:
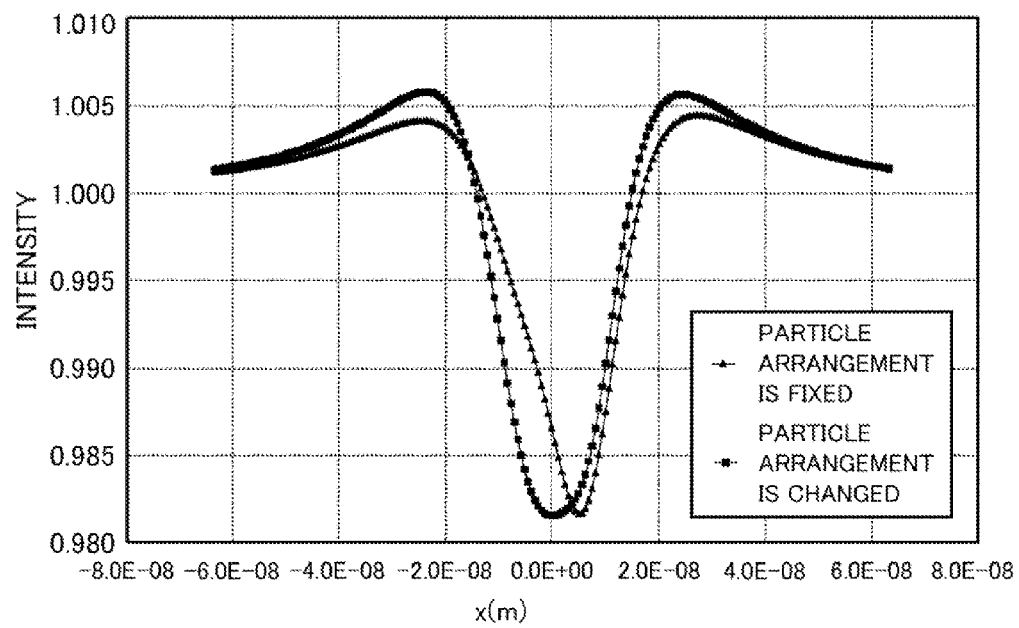
FIG. 10 is a diagram of illustrating intensities of scattered waves generated by the spherical nanoparticle cluster in the third embodiment.

FIGS. 8A and 8B are schematic diagrams of the scatterer and the spherical nanoparticle cluster in the present embodiment. FIG. 8A illustrates a scatterer 12 that has a cubic shape, and FIG. 8B illustrates a state in which a spherical nanoparticle cluster 14 (a plurality of spherical nanoparticles) is spread (arranged) inside a cubic region 13 that has the same shape and size as those of the scatterer 12. FIG. 9 is an arrangement diagram of the spherical nanoparticle cluster 14 in deriving the scattered wave. FIG. 10 is a diagram of illustrating intensities of the scattered waves generated by the spherical nanoparticle cluster 14. In FIG. 9, the incident wave 4 has an x polarization, and an observation line 5 in an x direction is set at a position distant from the spherical nanoparticle cluster 14 by 10 nm in a z direction. In such a condition, the scattered wave is derived by using the T-matrix method.

TABLE 4

| ONE SIDE (nm) OF SCATTERER (CUBE) | REFRACTIVE INDEX OF SPHERICAL NANOPARTICLE | RADIUS (nm) OF SPHERICAL NANO- PARTICLE | NUMBER OF SPHERICAL NANO- PARTICLES |
| --- | --- | --- | --- |
| 20.0 | 2.0 | 3.0 | 7 |

Table 4 indicates parameters that are used for the calculation in the present embodiment. The scatterer 12 is a cube having each side of 20 nm. The refractive index of the spherical nanoparticle that is spread is 2.0, the radius of the spherical nanoparticle is 3.0 nm, and the number of the spherical nanoparticles is 7, each of which is constant. As described in the second embodiment, in the derivation calculation of the scattered wave generated by the scatterer 12, the intensity of the electromagnetic field of the x polarization (the intensity of the scattered wave) is bilaterally symmetric with x=0. The intensity of the electromagnetic field in the x direction of the scattering generated by the spherical nanoparticle cluster 14 when a particle arrangement of the spherical nanoparticle cluster 14 is fixed is indicated as PARTICLE ARRANGEMENT IS FIXED in FIG. 10. The intensity of the electromagnetic field in the x direction of the scattering generated by the spherical nanoparticle cluster 14 when the particle arrangement of the spherical nanoparticle cluster 14 is changed five times and an average value of the five intensities is calculated is indicated as PARTICLE ARRANGEMENT IS CHANGED in FIG. 10. When the particle arrangement is fixed, the intensity of the electromagnetic field is bilaterally asymmetric with x=0. On the other hand, when the particle arrangement is changed to calculate the average value, the intensity is bilaterally symmetric with x=0.

Fourth Embodiment

Next, a fourth embodiment of the present invention will be described. The present embodiment arranges two scatterers to perform a derivation calculation of a multiple scattering. In other words, T-matrix of the scatterer is defined, and multiple scattered waves from the plurality of scatterers disposed at arbitrary positions are derived by using the T-matrix method. Therefore, according to the present embodiment, the multiple scattered waves from the plurality of scatterers can be derived at high speed.

Figures 11A, 11B:
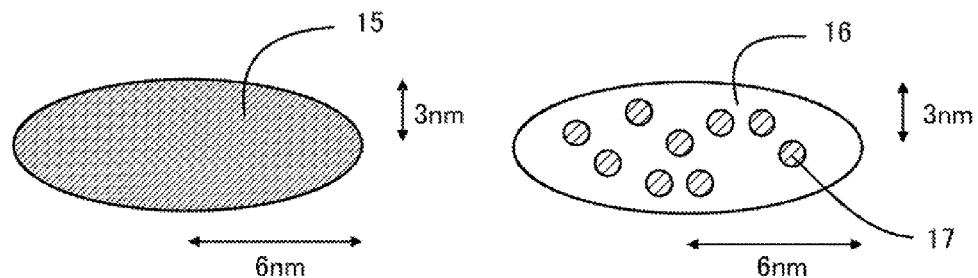
FIGS. 11A and 11B are schematic diagrams of a scatterer and a spherical nanoparticle cluster in a fourth embodiment.
Figure 12A:
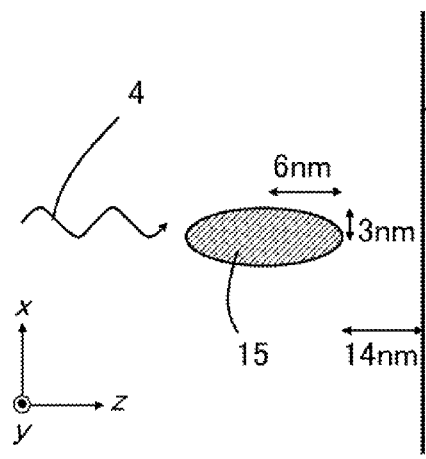
FIGS. 12A to 12B are arrangement diagrams of the scatterer and the spherical nanoparticle cluster in the fourth embodiment.
Figure 12B:
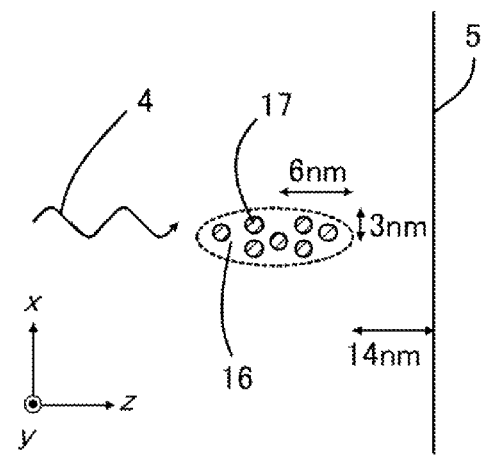
Figure 13:
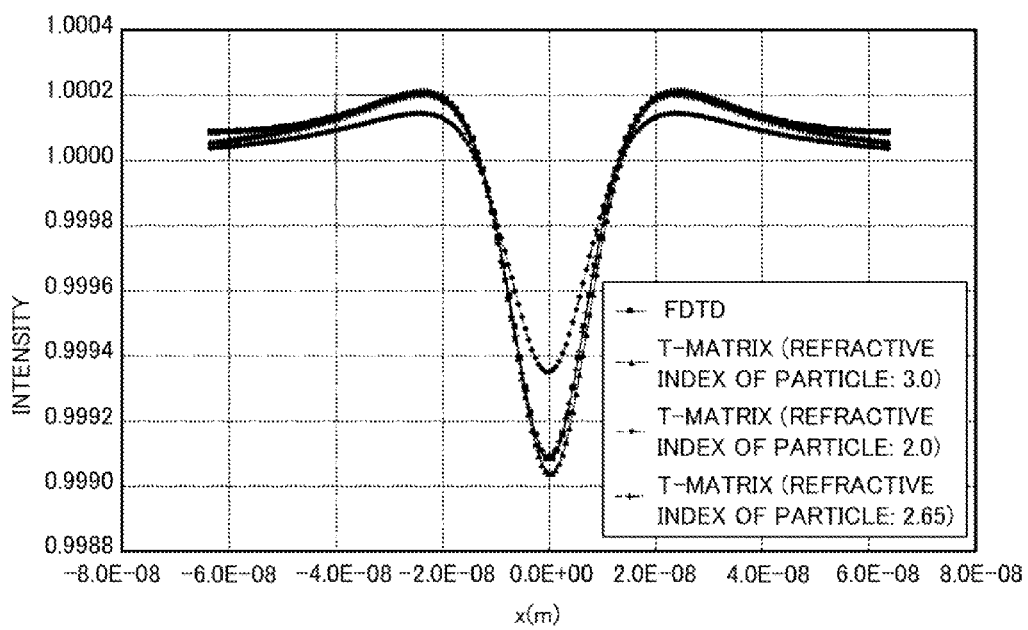
FIG. 13 is a diagram of illustrating intensities of scattered waves generated by the scatterer and the spherical nanoparticle cluster in the fourth embodiment.

FIGS. 11A and 11B are schematic diagrams of a scatterer and a spherical nanoparticle cluster in the present embodiment. FIG. 11A illustrates a scatterer 15 that has an elliptical shape, and FIG. 11B illustrates a state in which a spherical nanoparticle cluster 17 (a plurality of spherical nanoparticles) is spread (arranged) inside an elliptical region 16 having the same shape and size as those of the scatterer 15. FIGS. 12A and 12B are arrangement diagrams of the scatterer and the spherical nanoparticle cluster. FIG. 12A illustrates an arrangement in which the incident wave 4 (the electromagnetic wave) enters the scatterer 15 to perform the derivation calculation of the scattered wave, and FIG. 12B illustrates a state in which the scatterer 15 is replaced with the spherical nanoparticle cluster 17. FIG. 13 is a diagram of illustrating intensities of the scattered waves generated by the scatterer 15 and the spherical nanoparticle cluster 17.

In FIG. 12A, the incident wave 4 has an x polarization, and an observation line 5 in an x direction is set at a position distant from the scatterer 15 by 14 nm in a z direction. In the present embodiment, the intensity of the x component of the electromagnetic field on the observation line 5 is derived and calculated. In the present embodiment, the derivation calculation of the electromagnetic field is performed by using the FDTD method, but the embodiment is not limited to this and other methods may also be used. Next, FIG. 12B illustrates a case in which the scatterer 15 of FIG. 12A is replaced with the spherical nanoparticle cluster 17. In this arrangement, the electromagnetic field (the intensity of the scattered wave) on the observation field 5 is derived and calculated by using the T-matrix method.

Figure 14:
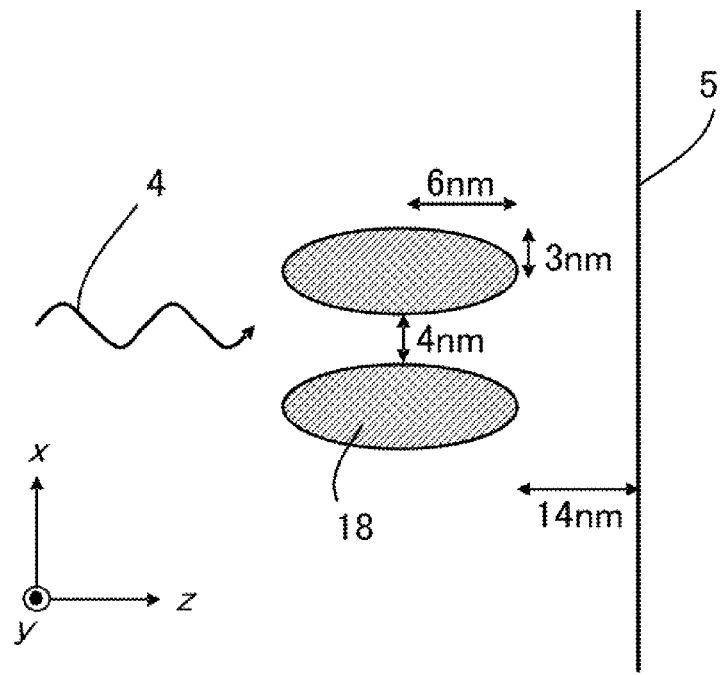
FIG. 14 is an arrangement diagram of two scatterers in the fourth embodiment.
Figure 15:
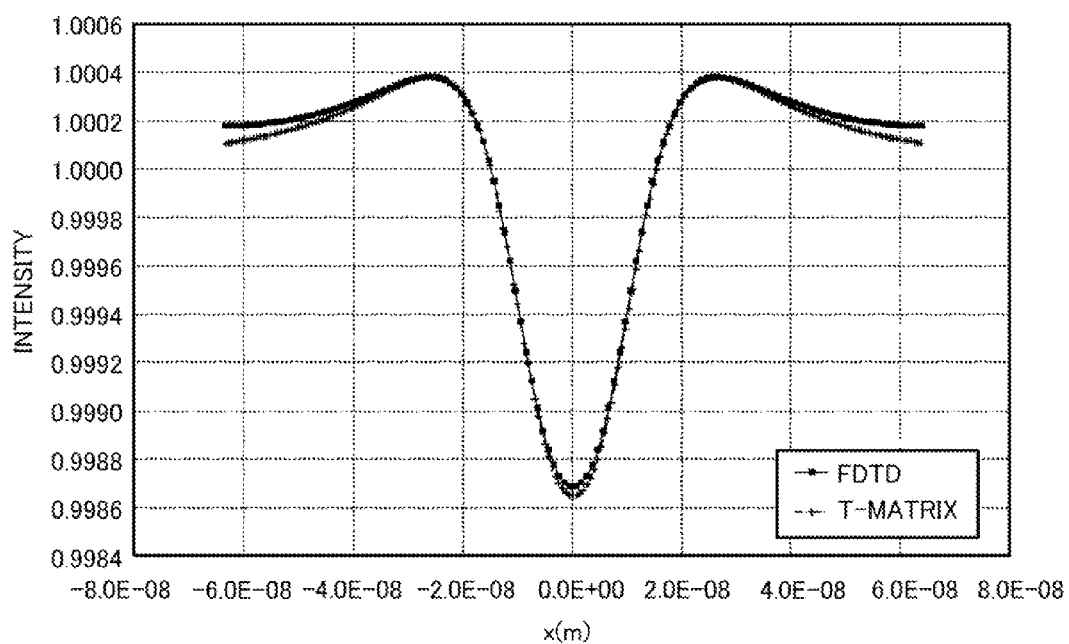
FIG. 15 is a diagram of illustrating intensities of the scattered waves generated by the two scatterers and the spherical nanoparticle cluster in the fourth embodiment.

FIG. 14 is an arrangement diagram of two scatterers 18. In FIG. 14, two scatterers 18 are arranged in the x direction, and a parameter setting when the intensity of the electromagnetic field (the intensity of the multiple scattered waves) of an x polarization is observed on the observation line 5 in the x direction distant by 14 nm in a z direction is illustrated. FIG. 15 illustrates the intensities of the scattered waves generated by the scatterer 18 and the spherical nanoparticle cluster 17.

In the present embodiment, the intensity of the x component of the electromagnetic field on the observation line 5 is derived and calculated. When the scatterer 15 is used as the scatterer 18, the derivation calculation of the electromagnetic field is performed by using the FDTD, but the embodiment is not limited to this and other methods may also be used. When the scatterer 18 is replaced with the spherical nanoparticle cluster 17, the derivation calculation is performed by using the T-matrix of the spherical nanoparticle cluster 17.

TABLE 5

| RADIUS (nm) OF MAJOR AXIS OF SCATTERER (ELLIPSOID) | RADIUS (nm) OF MINOR AXIS OF SCATTERER (ELLIPSOID) | RADIUS (nm) OF SPHERICAL NANO-PARTICLE | VOLUME FRACTION OF SPHERICAL NANOPARTICLE |
|---|---|---|---|
| 6.0 | 3.0 | 0.5 | 0.1 |

Table 5 indicates parameters that are used for the derivation calculation in the present embodiment. The scatterer 15 is an ellipsoid that has a major axis of 6.0 nm, a minor axis of 3.0 nm, and one side of 10 nm with a refractive index of 1.1. In this case, the intensity of the electromagnetic field (the intensity of the scattered wave generated by the scatterer) in the x direction of the scatterer 15 on the observation line 5 is indicated as FDTD in FIG. 13. In FIG. 12B, the process similar to that of the first embodiment is performed to derive and calculate the intensity of the electromagnetic field. In this case, the refractive index of the spherical nanoparticle is 2.65, which coincides with that of FDTD. The result is indicated as T-MATRIX (REFRACTIVE INDEX OF PARTICLE: 2.65) in FIG. 13.

Next, the intensity of the electromagnetic field of the x polarization on the observation line 5 when the two scatterers 18 are arranged in the x direction is indicated as FDTD in FIG. 15. The intensity of the electromagnetic field of the x polarization on the observation line 5, which is obtained by defining the T-matrix of the spherical nanoparticle cluster 17 as indicated by Table 5 and performing the multiple scattering derivation, is indicated as T-MATRIX in FIG. 15. In this case, the spherical nanoparticle cluster 17 has a radius of 0.5 nm, a volume fraction of 0.1, and a refractive index of 2.65. As illustrated in FIG. 15, the FDTD and the T-matrix coincide with each other.

TABLE 6

| | COMPUTER SPECIFICATION | CALCULATION TIME |
|---|---|---|
| FDTD | AMD Opteron254/2.8 GHz | 50 MINUTES 19 SECONDS |
| T-MATRIX | Dual-Core AMD Opteron ™ Processor 2220 2.8 GHz | 4 SECONDS |

Table 6 indicates a specification of the computer that is used for deriving the electromagnetic field and a time required for deriving the electromagnetic field in the present embodiment. The derivation time required by defining the T-matrix of the scatterer 15 is 750 times as fast as the derivation time by the FDTD. However, this derivation time does not include a time required for calculating the T-matrix of the scatterer 15. Thus, once the T-matrix of the scatterer is calculated, a high-speed derivation can be performed compared to the FDTD when the multiple scattering of the scatterer is calculated.

According to each of the above embodiments, a method of deriving a scattered wave that is capable of deriving the scattered wave from the scatterer having an arbitrary shape at high speed and with high accuracy can be provided. The derivation method of each embodiment is, for example, suitably used for manufacturing a lens (a scatterer) that contains a nanoparticle. In such a lens, it is preferred that the lens be designed so that an undesired scattered wave is not emitted from the nanoparticle in the lens. A method of manufacturing a lens with high accuracy can be provided by applying the derivation method of each embodiment to the lens as a scatterer. In addition, each of the above embodiments can also provide a non-transitory recording medium that records a program that is configured so that the method of deriving the scattered wave is executed by a computer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-091905, filed on Apr. 18, 2011, which is hereby incorporated by reference herein in its entirety.

What is claimed is:

1. A computer implemented method of deriving a scattered wave comprising the steps of:
   calculating, using a computer, a first scattered wave from a scatterer at a predetermined position by using a predetermined electromagnetic wave entering the scatterer;
   calculating, using the computer, a second scattered wave from a spherical nanoparticle cluster at the predetermined position by using T-matrix method when the predetermined electromagnetic wave enters the spherical nanoparticle cluster in a state where the spherical nanoparticle cluster containing a plurality of spherical nanoparticles is arranged inside a region that has the same shape and size as those of the scatterer;
   determining, using the computer, a condition of the plurality of spherical nanoparticles so that the first scattered wave is equal to the second scattered wave; and obtaining, using the computer, the scattered wave from the scatterer at an arbitrary position when an arbitrary electromagnetic wave enters the scatterer, based on the determined condition of the plurality of spherical nanoparticles.

2. The method according to claim 1,
wherein the condition of the plurality of spherical nanoparticles is any one or a combination of two or more of conditions related to a radius of each spherical nanoparticle, a number of the spherical nanoparticles, and a refractive index of each spherical nanoparticle.

3. The method according to claim 2,
wherein the radius of the spherical nanoparticle is determined so that the second scattered wave does not change when the radius of the spherical nanoparticle is reduced and the number of the spherical nanoparticles is increased in a state where a volume fraction of the spherical nanoparticle cluster with respect to a volume of the region is constant, and
wherein an initial value of the refractive index of the spherical nanoparticle is set so that an effective refractive index determined by the refractive index of the spherical nanoparticle and the volume fraction coincides with a refractive index of the scatterer.

4. The method according to claim 1,
wherein the spherical nanoparticle cluster contains at least one of a first spherical nanoparticle and a second spherical nanoparticle larger than the first spherical nanoparticle.

5. The method according to claim 1,
wherein the spherical nanoparticle cluster is arranged multiple times at random,
wherein an average value of scattered waves from the spherical nanoparticle cluster is calculated by using the T-matrix method, and
wherein the average value is used as the second scattered wave.

6. The method according to claim 1,
wherein T-matrix of the scatterer is defined, and
wherein multiple scattered waves from a plurality of scatterers arranged at arbitrary positions are derived by using the T-matrix method.

7. A method of manufacturing a lens containing a nanoparticle, comprising the step of deriving a scattered wave of the lens containing the nanoparticle as a scatterer by using a method of deriving the scattered wave comprising the steps of:
calculating, using a computer, a first scattered wave from a scatterer at a predetermined position by using a predetermined electromagnetic wave entering the scatterer;
calculating, using the computer, a second scattered wave from a spherical nanoparticle cluster at the predetermined position by using T-matrix method when the predetermined electromagnetic wave enters the spherical nanoparticle cluster in a state where the spherical nanoparticle cluster containing a plurality of spherical nanoparticles is arranged inside a region that has the same shape and size as those of the scatterer;
determining, using the computer, a condition of the plurality of spherical nanoparticles so that the first scattered wave is equal to the second scattered wave; and
obtaining, using the computer, the scattered wave from the scatterer at an arbitrary position when an arbitrary electromagnetic wave enters the scatterer, based on the determined condition of the plurality of spherical nanoparticles.

8. A non-transitory recording medium that records a program that is configured so that a method of deriving a scattered wave is executed by a computer, the method of deriving the scattered wave comprising the steps of:
calculating a first scattered wave from a scatterer at a predetermined position by using a predetermined electromagnetic wave entering the scatterer;
calculating a second scattered wave from a spherical nanoparticle cluster at the predetermined position by using T-matrix method when the predetermined electromagnetic wave enters the spherical nanoparticle cluster in a state where the spherical nanoparticle cluster containing a plurality of spherical nanoparticles is arranged inside a region that has the same shape and size as those of the scatterer;
determining a condition of the plurality of spherical nanoparticles so that the first scattered wave is equal to the second scattered wave; and
obtaining the scattered wave from the scatterer at an arbitrary position when an arbitrary electromagnetic wave enters the scatterer, based on the determined condition of the plurality of spherical nanoparticles.

* * * * *